(12) United States Patent
Matsumoto (10) Patent No.: US 9,970,887 B2
(45) Date of Patent: May 15, 2018

(54) DEFECT INSPECTION METHOD AND APPARATUS THEREFOR

(71) Applicant: HONDA MOTOR CO., LTD., Tokyo (JP)

(72) Inventor: Junichi Matsumoto, Tochigi-ken (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days. days.

(21) Appl. No.: 15/613,435

(22) Filed: Jun. 5, 2017

(65) Prior Publication Data
US 2017/0356856 A1 Dec. 14, 2017

(30) Foreign Application Priority Data
Jun. 9, 2016 (JP) .................. 2016-115498

(51) Int. Cl.
| | |
|---|---|
| *G01N 21/956* | (2006.01) |
| *G01B 11/30* | (2006.01) |
| *G01N 21/88* | (2006.01) |
| *G02B 26/02* | (2006.01) |
| *G06T 5/50* | (2006.01) |
| *G06T 7/00* | (2017.01) |

(52) U.S. Cl.
CPC .......... *G01N 21/956* (2013.01); *G01B 11/30* (2013.01); *G01N 21/8851* (2013.01); *G02B 26/02* (2013.01); *G06T 5/50* (2013.01); *G06T 7/0004* (2013.01)

(58) Field of Classification Search
CPC ............. G01N 21/956; G01N 21/8806; G01N 21/8851; G01B 11/30; G06T 5/50; G06T 7/0004
USPC ....................................................... 356/237.2
See application file for complete search history.

(56) References Cited

U.S. PATENT DOCUMENTS

| | | | | |
|---|---|---|---|---|
| 5,060,118 A | * | 10/1991 | Penrod ...................... | F21V 9/02 356/230 |
| 5,237,404 A | * | 8/1993 | Tanaka .................. | G01B 11/303 348/128 |
| 5,309,222 A | * | 5/1994 | Kamei ............... | G01B 11/2527 356/613 |
| 5,414,518 A | * | 5/1995 | Yazejian ............ | G01N 21/8803 356/237.2 |

(Continued)

FOREIGN PATENT DOCUMENTS

| | | |
|---|---|---|
| JP | 08-086633 | 4/1996 |
| JP | 09-210922 | 8/1997 |
| JP | 2014-066657 | 4/2014 |

*Primary Examiner* — Roy M Punnoose
(74) *Attorney, Agent, or Firm* — Rankin, Hill & Clark LLP (57) ABSTRACT

Slit light is irradiated onto an object to be photographed (for example, an automobile body) in order to obtain a source image. Next, either one of a maximum value filtering process or a minimum value filtering process is performed on the source image to thereby obtain a first filter-processed image. Furthermore, after obtaining a second filter-processed image by carrying out a remaining one of the minimum value filtering process or the maximum value filtering process with respect to the first filter-processed image, a difference is determined between the second filter-processed image and the source image, and a difference image is obtained. Thereafter, a binarization process is implemented with respect to the difference image.

6 Claims, 11 Drawing Sheets

(56) References Cited

U.S. PATENT DOCUMENTS

| | | | | |
|---|---|---|---|---|
| 5,436,726 A * | 7/1995 | Ventura | ............... | G01B 11/25 356/237.2 |
| 5,636,024 A * | 6/1997 | Crookham | ........... | G01M 11/005 356/237.1 |
| 5,726,705 A * | 3/1998 | Imanishi | ............ | G01N 21/8806 348/92 |
| 5,734,742 A * | 3/1998 | Asaeda | ............... | G01N 21/88 382/107 |
| 6,266,138 B1 * | 7/2001 | Keshavmurthy | .... | G01B 11/303 356/237.2 |
| 2008/0144044 A1 * | 6/2008 | Ehrick | ............... | G01B 11/25 356/610 |
| 2009/0290781 A1 * | 11/2009 | Yannick | ............ | G01N 21/8806 382/141 |
| 2012/0133761 A1 * | 5/2012 | Cho | ............... | H04N 7/18 348/92 |
| 2015/0204797 A1 * | 7/2015 | Colle | ............... | G01N 21/90 356/239.4 |
| 2017/0108443 A1 * | 4/2017 | Kurihara | ............ | G01N 21/8806 |

* cited by examiner

DEFECT INSPECTION METHOD AND APPARATUS THEREFOR

CROSS-REFERENCE TO RELATED APPLICATION

This application is based upon and claims the benefit of priority from Japanese Patent Application No. 2016-115498 filed on Jun. 9, 2016, the contents of which are incorporated herein by reference.

BACKGROUND OF THE INVENTION

Field of the Invention

The present invention relates to a defect inspection method and an apparatus therefor, for inspecting whether or not a defect exists on an object to be photographed by irradiating the object to be photographed with striped illumination.

Description of the Related Art

In a manufacturing process for manufacturing automobile bodies, painting is performed on the automobile bodies. Consequently, a coating film is provided. In this instance, protrusions on the order of several tens of μm, or stated otherwise, painting defects may be formed in the coating film. If such painting defects are formed and remain as is, the aesthetic appearance of the automobile body is impaired. For this reason, after formation of the coating film, an inspection is performed in order to determine whether or not such painting defects are present.

As a defect inspection apparatus for performing this type of defect inspection, a defect inspection apparatus is known by which a striped contrast pattern (striped illumination) is irradiated, as described in Japanese Laid-Open Patent Publication 09-210922. In such a technique, on an object to be photographed, a location irradiated with the contrast pattern is photographed by a camera, and it is determined whether or not a defect exists by carrying out image processing with respect to an obtained source image.

Further, in Japanese Laid-Open Patent Publication No. 2014-066657, a technique is proposed whereby an image in which a defect does not exist in the source image is taken as a master image, and the presence or absence of scratches on a painted surface is determined by taking a difference between the master image and a captured image of the inspection site.

SUMMARY OF THE INVENTION

In an inspection station, after an automobile body on which a paint defect inspection has been completed is conveyed out, an automobile body to be inspected next is conveyed into the inspection station. In this case, the position of the outwardly conveyed automobile body frequently does not coincide with the position of the inwardly conveyed automobile body.

When implementing the method described in Japanese Laid-Open Patent Publication No. 09-210922, if there are variations in the distance or the relative positioning between the object to be photographed and the irradiating device and the camera, a variation also occurs in bright and dark differences of the contrast pattern. Such a variation is a possible cause of an erroneous determination of the presence or absence of a defect. However, as noted above, since the positions of automobile bodies at the inspection station do not necessarily coincide every time, it is necessary to make a correction when such a positional deviation occurs. Thus, additional time is required to analyze the image.

Further, in order to implement the method of Japanese Laid-Open Patent Publication No. 2014-066657, it is necessary to prepare and create the master image in advance. In the foregoing manner, with the defect inspection techniques according to the conventional art, making an efficient judgment as to whether or not a defect exists is not easy.

A principal object of the present invention is to provide a defect inspection method in which, while being a simple process, a determination as to whether or not a defect exists can be performed efficiently and with high reliability.

Another object of the present invention is to provide a defect inspection apparatus for implementing the aforementioned defect inspection method.

According to an embodiment of the present invention, a defect inspection method is provided for inspecting whether or not a defect exists on an object to be photographed, by irradiating striped illumination with respect to the object to be photographed, and based on an image obtained from the object to be photographed, the method comprising the steps of:

irradiating striped illumination on the object to be photographed from a striped illumination irradiating unit;

photographing, by an image capturing unit, the object to be photographed which is irradiated with the striped illumination, and obtaining a source image;

obtaining a first filter-processed image by a first filtering process that carries out either one of a maximum value filtering process or a minimum value filtering process with respect to the source image;

obtaining a second filter-processed image by a second filtering process that carries out a remaining one of the minimum value filtering process or the maximum value filtering process with respect to the first filter-processed image;

obtaining a difference image in which a difference from the source image is determined using the second filter-processed image as a background image; and performing a binarization process with respect to the difference image, and obtaining a binarized image for determining whether or not a defect exists within an imaging range.

Further, according to an embodiment of the present invention, a defect inspection apparatus is provided, which is adapted to inspect whether or not a defect exists on an object to be photographed, by irradiating striped illumination with respect to the object to be photographed, and based on an image obtained from the object to be photographed, the apparatus comprising:

a striped illumination irradiating unit adapted to irradiate the object to be photographed with striped illumination;

an image capturing unit adapted to photograph the object to be photographed which is irradiated with the striped illumination;

an image analysis processing unit adapted to carry out an image analysis process with respect to a source image obtained by the image capturing unit; and a displacement device adapted to displace the striped illumination irradiating unit and the image capturing unit;

wherein the image analysis processing unit performs a first filtering process to obtain a first filter-processed image by carrying out either one of a maximum value filtering process or a minimum value filtering process with respect to the source image, a second filtering process to obtain a second filter-processed image by carrying out a remaining one of the minimum value filtering process or the maximum value filtering process with respect to the first filter-processed image, a differentiating process to obtain a difference image in which a difference from the source image is determined using the second filter-processed image as a background image, and a binarization process with respect to the difference image.

In the foregoing manner, according to the present invention, the maximum value filtering process and the minimum value filtering process are carried out continuously with respect to the source image. In this instance, the order in which the maximum value filtering process and the minimum value filtering process are performed is not particularly limited, and either one of them may be performed first.

Along with continuously carrying out the maximum value filtering process and the minimum value filtering process, any luminance based on defects is largely eliminated. Therefore, the second filter-processed image, which is obtained through such filtering processes, is a contrast pattern (grayscale image) in which a background texture of the object to be photographed appears. Consequently, by treating the second filter-processed image as a background image and subtracting the source image portion therefrom (obtaining the difference between the second filter-processed image and the source image), a difference image in which defects are emphasized can be obtained.

By carrying out the binarization process based on the difference image, a binarized image is obtained. On the basis of the binarized image, it can easily be determined whether or not a defect exists.

In the foregoing manner, according to the present invention, the source image is created from a photographed location of the object to be photographed, a two-stage filtering process is performed on the source image in order to obtain a background image, and the source image portion is subtracted from the background image. Consequently, the photographed location of the source image coincides with the photographed location of the second filter-processed image which has undergone the two-stage filtering process.

Therefore, in the case that the object to be photographed, for example, is an automobile body conveyed into the inspection station, regardless of whether or not the automobile body is shifted in position from a previous inspection position, and without performing any corrections, it is possible to determine whether or not a defect exists. In addition, there is no need to prepare a master image in advance that serves as a reference background. Consequently, the image analysis process proceeds efficiently.

Further, the binarization process can be performed with high accuracy. This is because, as noted previously, the photographed location of the source image coincides with the photographed location of the second filter-processed image which has undergone the two-stage filtering process. Consequently, it can be determined highly accurately whether or not a defect exists.

The first filtering process may be performed a plurality of times. In this case, the number of times that the second filtering process is performed is the same as the number of times that the first filtering process is performed. More specifically, when the maximum value filtering process as the first filtering process, and the minimum value filtering process as the second filtering process are carried out, after the maximum value filtering process has been performed continuously a plurality of times, the minimum value filtering process is performed continuously a plurality of times. In addition, the number of times that the minimum value filtering process is performed is the same as the number of times that the maximum value filtering process is performed.

By carrying out the above processes, a difference image can be obtained in which a luminance based on the defect appears more clearly. Accordingly, it becomes easier to make a confirmation of the presence or absence of a defect.

In the event that the first filtering process and the second filtering process are performed a plurality of times, the number of times that each process is executed is two times or more. This is because, in this case, the luminance based on the defect appears more clearly than if the number of times that the processes are executed is one time only. Most preferably, the number of times that the processes are executed is three times.

According to the present invention, the source image is created from a photographed location of the object to be photographed, whereas the second filter-processed image is obtained by carrying out the maximum value filtering process and the minimum value filtering process with respect to the source image, and the second filter-processed image is treated as a background image and the source image is subtracted therefrom. Therefore, since the photographed location of the source image coincides with the photographed location of the second filter-processed image, there is no need to prepare a master image in advance that serves as a reference background.

Further, regardless of whether the object to be photographed is in a position that coincides with the previous inspection position or is in a different position, or stated otherwise, regardless of whether or not positional shifting has taken place, without performing any corrections, it is still possible to determine whether or not a defect exists. For the reasons mentioned above, the image analysis process proceeds efficiently.

Further, as noted previously, because the photographed location of the source image coincides with the photographed location of the second filter-processed image which has undergone the two-stage filtering process, the binarization process can be performed with high accuracy. Consequently, it can be determined highly accurately whether or not a defect exists.

The above and other objects, features, and advantages of the present invention will become more apparent from the following description when taken in conjunction with the accompanying drawings, in which preferred embodiments of the present invention are shown by way of illustrative example.

DESCRIPTION OF THE PREFERRED EMBODIMENTS

Preferred embodiments in relation to a defect inspection method according to the present invention, and a defect inspection apparatus for implementing such a method will be described in detail below with reference to the accompanying drawings.

Figure 1:
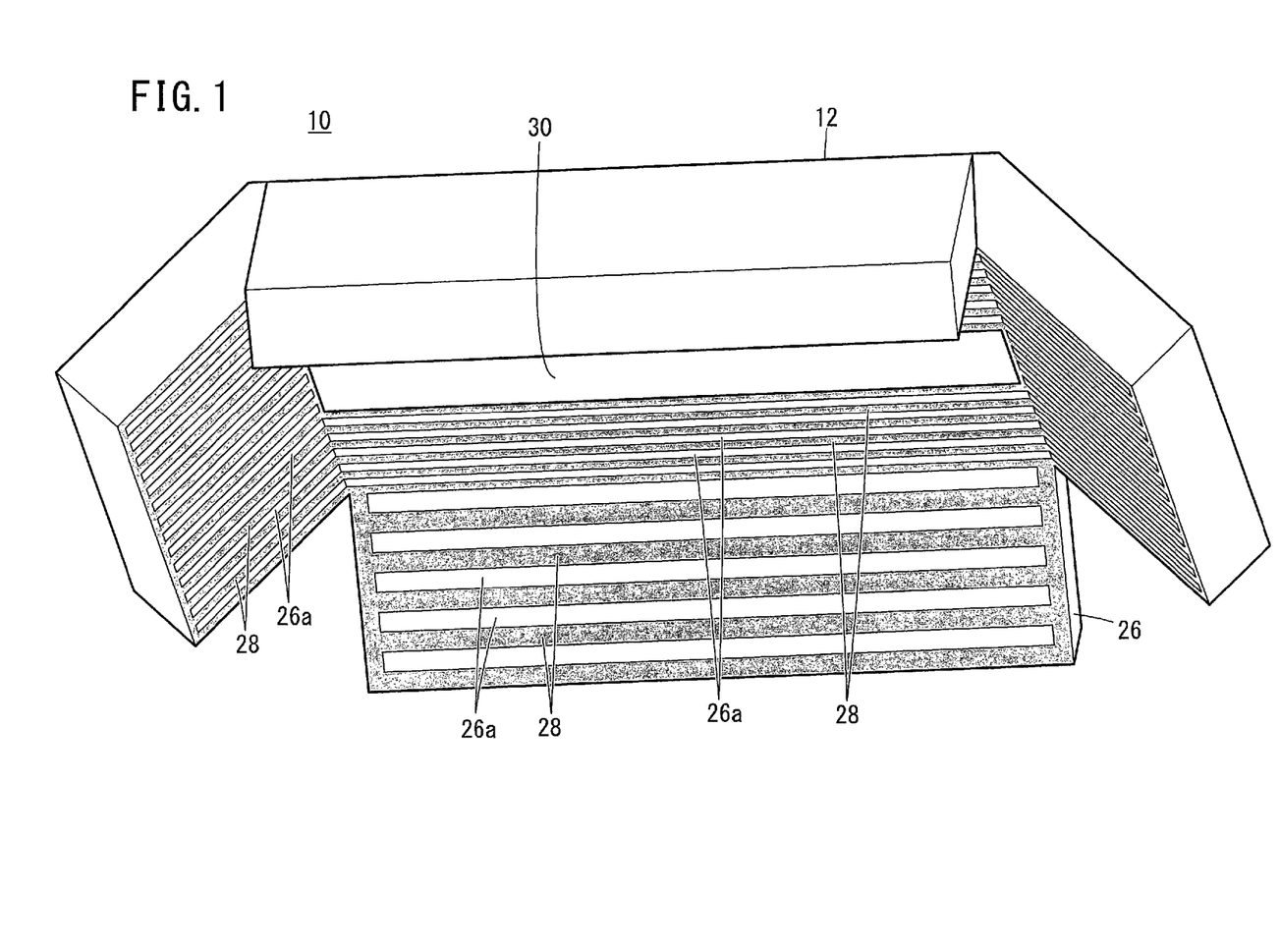
FIG. 1 is a schematic perspective view showing principal parts of a machine base that constitutes part of a defect inspection apparatus according to an embodiment of the present invention.
Figure 2:
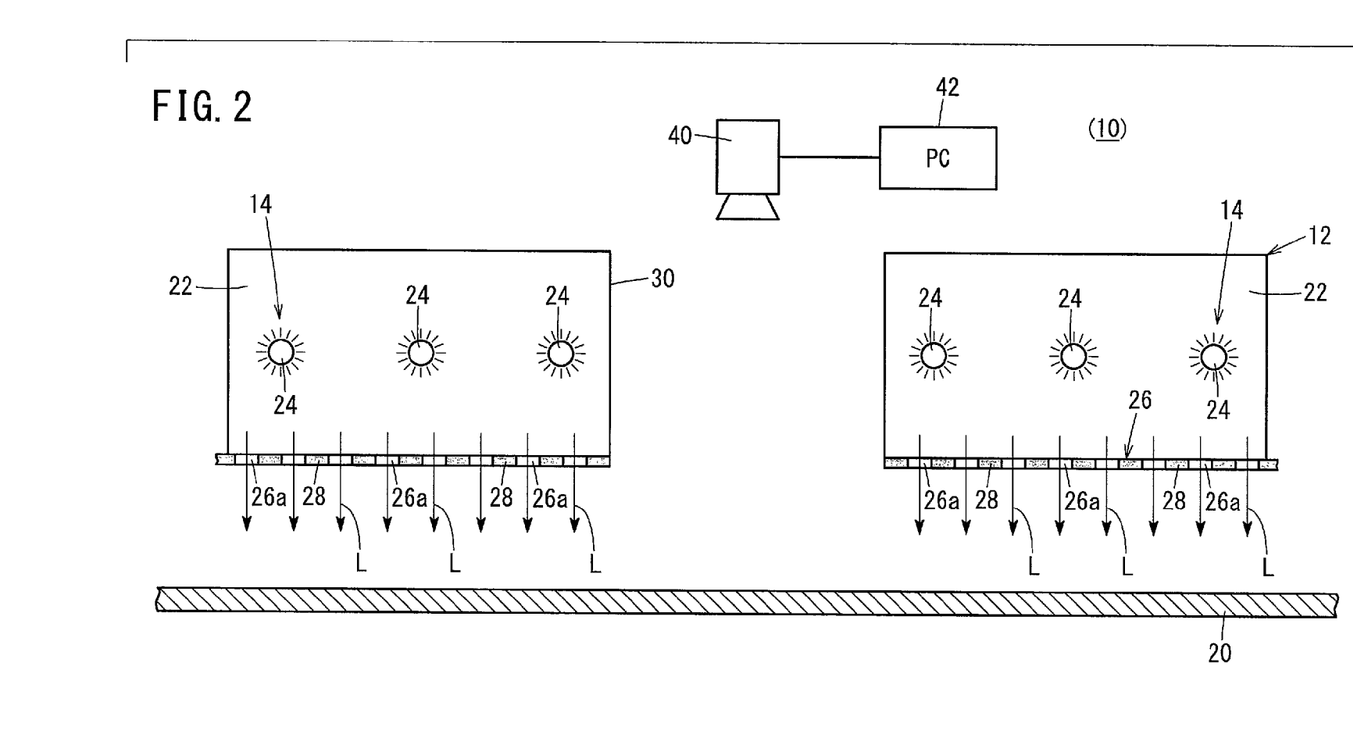
FIG. 2 is a schematic vertical cross-sectional view of principal parts of the defect inspection apparatus including the machine base shown in FIG. 1.

FIG. 1 is a schematic perspective view showing principal parts of a machine base 12 that constitutes part of a defect inspection apparatus 10 according to an embodiment of the present invention, and FIG. 2 is a schematic vertical cross-sectional view of principal parts of the defect inspection apparatus 10. The defect inspection apparatus 10 includes the machine base 12, and a slit light source 14 (striped illumination irradiating unit) disposed on the machine base 12. Slit light L (striped illumination) is irradiated from the slit light source 14 onto an automobile body 20 which is an object to be photographed.

As shown in FIG. 2, on the machine base 12, an accommodating chamber 22 is formed on a lower side facing toward the automobile body 20, and a plurality of individual white light emitting diodes (white LEDs) 24 are accommodated in the accommodating chamber 22. The slit light source 14 is constituted by the white LEDs 24. Light emitted by the white LEDs 24 passes through translucent portions 26a of a translucent cover 26, and proceeds vertically downward toward the side of the automobile body 20.

A plurality of individual light shielding lines 28 are provided in a striped shape or pattern on the translucent cover 26. Light emitted by the white LEDs 24 is blocked at locations where the light shielding lines 28 exist. For this reason, the light that is incident on the automobile body 20 has a slit shape (striped shape). Stated otherwise, slit light L is obtained.

A through hole 30 having a substantially rectangular cross section is formed substantially in the center of the machine base 12 along a thickness direction, or in other words, along a vertical direction thereof. Of course, the white LEDs 24 do not exist at the location where the through hole 30 is formed.

A camera 40 serving as an image capturing device is disposed in the machine base 12 through a non-illustrated support frame (not shown) at a position above the through hole 30. Via the through hole 30, the camera 40 photographs or captures an image of a location that is irradiated with the slit light L.

Images captured by the camera 40 are transmitted to a computer 42 that functions as an image analysis processing unit. The computer 42 carries out an image analysis, to be described later, and on the basis of the results of such an analysis, a determination is made as to whether or not a defect exists.

In the above configuration, the machine base 12 and the camera 40 are displaced integrally by a non-illustrated displacement device (for example, and actuator or the like). Consequently, the location irradiated with the slit light L and the location photographed by the camera 40 change continuously.

The defect inspection apparatus 10 according to the present embodiment is constructed basically in the manner described above. Next, operations and effects of the defect inspection apparatus 10 will be described in relation to a defect inspection method according to the present embodiment.

Figure 4:
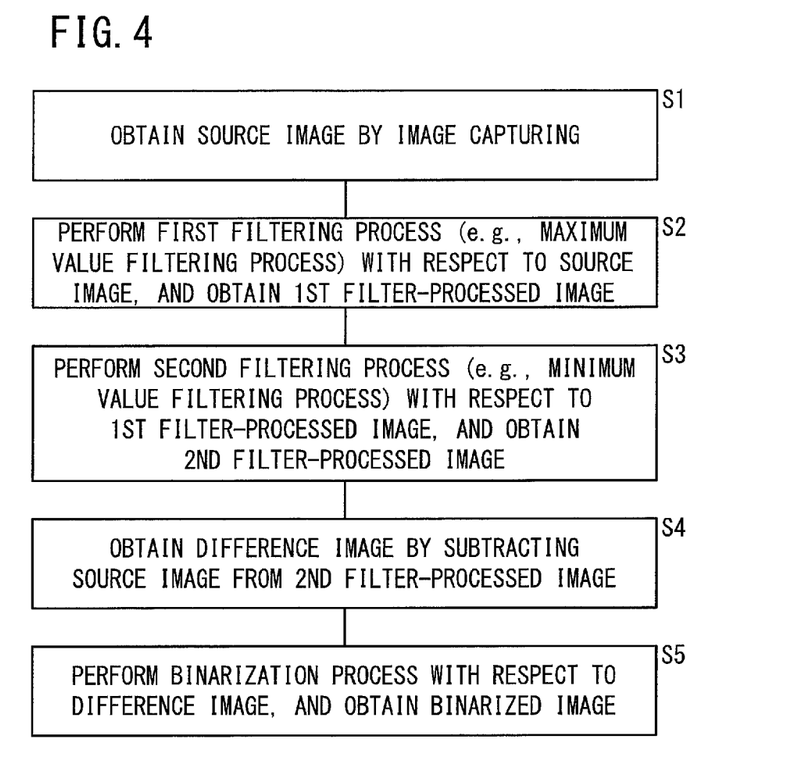
FIG. 4 is an outline flowchart of a defect inspection method according to an embodiment of the present invention.

FIG. 4 is an outline flowchart of a defect inspection method according to the present embodiment. The defect inspection method is roughly divided into a source image obtaining step S1, a first filter-processed image obtaining step S2, a second filter-processed image obtaining step S3, a difference image obtaining step S4, and a binarized image obtaining step S5.

In order to determine whether or not a painting defect exists on the automobile body 20 to which paint has been applied, the displacement device is energized, and the machine base 12 is positioned at a predetermined location of the automobile body 20. Thereafter, or prior to such displacement, the slit light source 14 is turned on.

Figure 3:
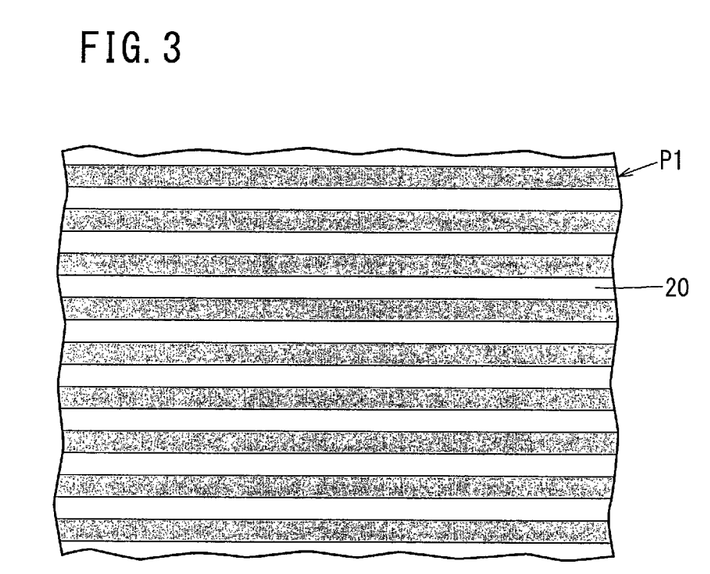
FIG. 3 is a plan view showing a striped contrast pattern that is formed on an automobile body as an object to be photographed.

A portion of the light emitted from the slit light source 14 passes through the translucent portions 26a of the translucent cover 26, and a portion of such light is blocked by the light shielding lines 28. Consequently, the slit light L is formed, and the slit light L is made incident on the automobile body 20 in a vertically downward direction. As a result, a stripe shaped contrast pattern P1 is formed, as shown in FIG. 3.

Figure 5:
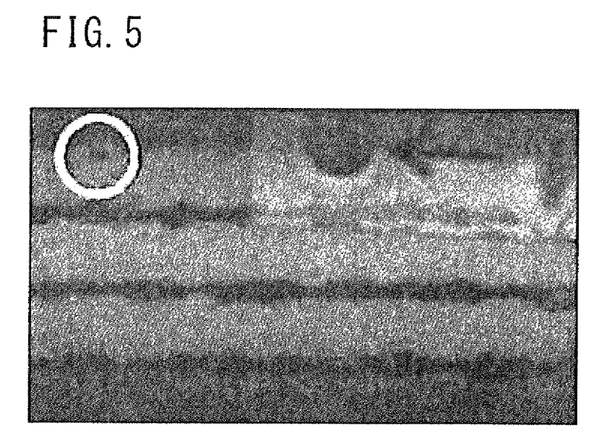
FIG. 5 is a source image obtained by photographing with a camera a location on the automobile body which is irradiated with slit light.

The camera 40 captures an image of the contrast pattern P1, and transmits the captured image as image information to the computer 42. More specifically, on the basis of such image information, the computer 42 obtains the source image shown in FIG. 5 (step S1 of FIG. 4). In FIG. 5, the location surrounded by the circle is a painting defect.

Next, the computer 42 carries out a first filtering process, and a second filtering process with respect to the source image. More specifically, either one of a maximum value filtering process or a minimum value filtering process is carried out initially, and next, a remaining one of the minimum value filtering process or the maximum value filtering process is carried out. Herein, a case will be exemplified in which the maximum value filtering process is performed as the first filtering process, and the minimum value filtering process is performed as the second filtering process.

Figure 6:
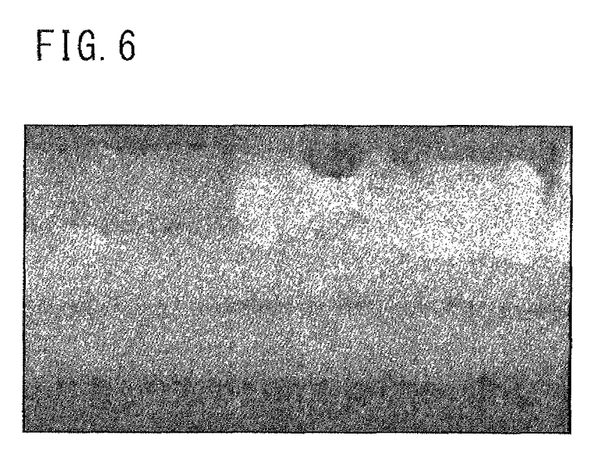
FIG. 6 is a maximum value filter-processed image (first filter-processed image) obtained by performing a maximum value filtering process (first filtering process) with respect to the source image of FIG. 5.

As is well known, according to the maximum value filtering process, the density value of a target pixel is taken as the maximum value of the density values of neighboring pixels. By this process of image analysis, a maximum value filter-processed image (first filter-processed image) as shown in FIG. 6 is obtained (step S2 in FIG. 4).

Figure 7:
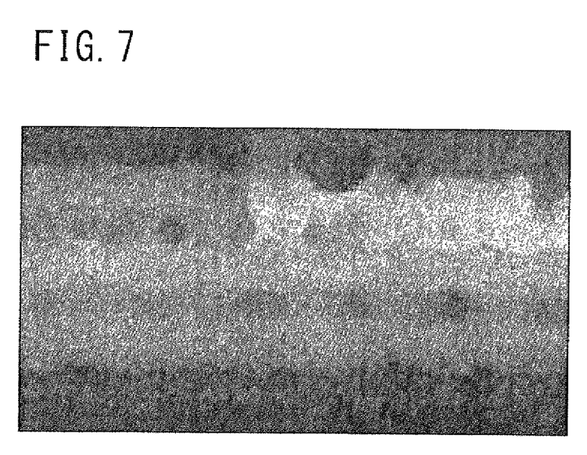
FIG. 7 is a minimum value filter-processed image (second filter-processed image) obtained by performing a minimum value filtering process (second filtering process) with respect to the maximum value filter-processed image (first filter-processed image) of FIG. 6.

Next, the minimum value filtering process is performed with respect to the maximum value filter-processed image. In this case, since the density value of the target pixel is taken as the minimum value of the density values of neighboring pixels, a minimum value filter-processed image (second filter-processed image) as shown in FIG. 7 is obtained (step S3 in FIG. 4). In this manner, in the minimum value filter-processed image, which is obtained by carrying out a two-stage filtering process, luminance based on defects is largely eliminated, and a background texture of the automobile body 20 appears.

Figure 8:
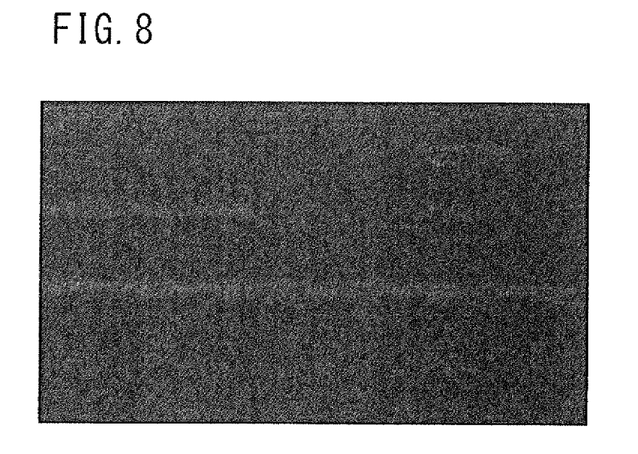
FIG. 8 is a difference image determined by subtracting the source image of FIG. 5 from the minimum value filter-processed image (second filter-processed image) of FIG. 7.

Next, the computer 42 treats the minimum value filter-processed image as a background image, and subtracts the source image portion therefrom. Stated otherwise, a difference between the minimum value filter-processed image and the source image is determined. Owing thereto, the difference image shown in FIG. 8 is obtained (step S4 in FIG. 4). The source image is an image in which the background texture of the automobile body 20 and painting defects are both reflected, whereas the minimum value filter-processed image is an image in which only the background texture of the automobile body 20 appears. Consequently, in the difference image, the background texture of the automobile body 20, which defines the background thereof, is substantially eliminated, and painting defects are emphasized.

Figure 9:
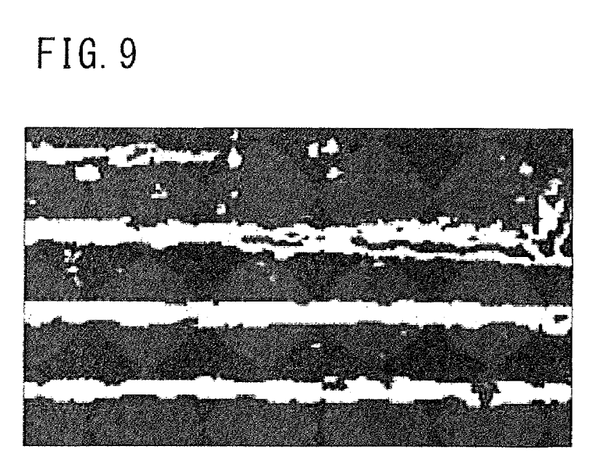
FIG. 9 is a binarized image obtained by performing a binarization process with respect to the difference image of FIG. 8.

Next, a binarization process is carried out with respect to the difference image, which was obtained in the manner described above. Consequently, as shown in FIG. 9, a binarized image is obtained in which painting defects are emphasized (step S5 in FIG. 4).

As may be necessary, a noise removal process and an area filter labeling process are performed with respect to the binarized image. In the noise removal process, linear white regions in the binarized image are eliminated. Further, in the area filter labeling process, white regions having areas less than or equal to a predetermined threshold value, and white regions having areas greater than or equal to a predetermined threshold value are eliminated, so that ultimately, only white regions having areas lying within a predetermined range remain.

Figure 10:
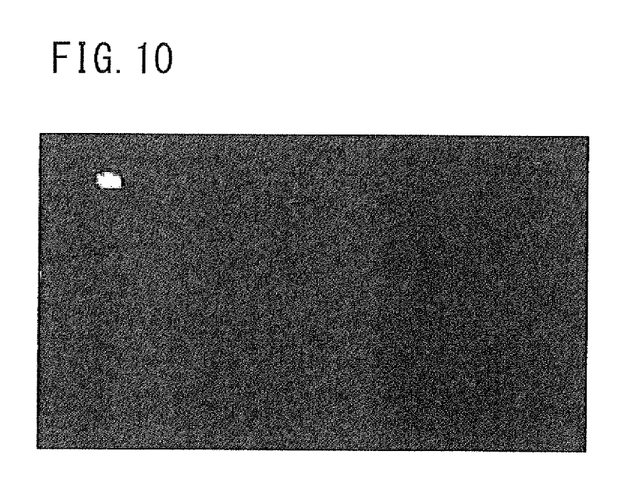
FIG. 10 is an image obtained by carrying out an area filter labeling process with respect to the binarized image of FIG. 9.
Figure 11:
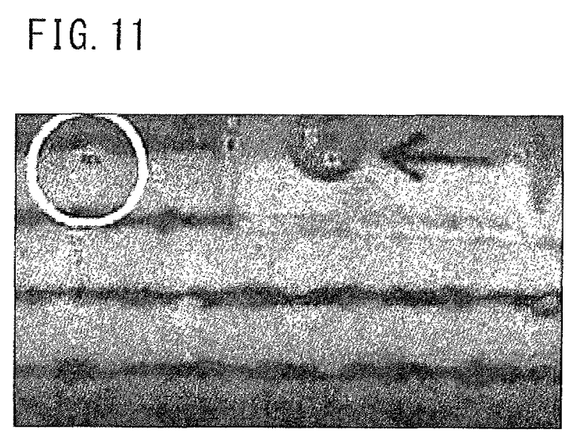
FIG. 11 is a diagnostic image for determining whether or not a defect exists.

The image after having carried out the area filter labeling process thereon is shown in FIG. 10, and a finally obtained diagnostic image is shown in FIG. 11. From FIGS. 10 and 11, it can be understood that painting defects are easily recognizable.

Further, as can be appreciated from the above, in the present embodiment, a difference may be taken between the source image, in which a location is photographed on which slit light L is irradiated of an automobile body 20 that has been conveyed into an inspection station, and a filter-processed image, in which a two-stage filtering process was carried out with respect to the source image. Consequently, even if the automobile body 20 undergoes a positional deviation with respect to an automobile body 20 that has been inspected previously, there is no need to perform a correction thereon. Therefore, the image analysis process proceeds efficiently. Moreover, because the photographed location of the source image coincides with the photographed location of the filter-processed image, the binarization process can be performed with high accuracy.

In addition, according to the present embodiment, there is no need to prepare a master image in advance that serves as a reference background. Due to this feature as well, the image analysis process proceeds efficiently. For the reasons described above, it is possible to efficiently and accurately determine whether or not protrusions are present in the form of painting defects.

The displacement device displaces the machine base 12 continuously. Accompanying displacement of the machine base 12, the slit light source 14 and the camera 40 also are displaced integrally therewith. Accordingly, the location irradiated with the slit light L and the location photographed by the camera 40, or stated otherwise, the inspection location, changes. As a result, inspection of defects can be implemented over a wide area of the automobile body 20.

When a protuberance is determined to be present within the contrast pattern P1, for example, a predetermined marking process is performed with respect to the protuberance. If the number of protuberances is small, the protuberances are removed by grinding or the like. On the other hand, if the number of protuberances is large, it may be preferable to perform repainting of the automobile body 20. In the foregoing manner, an automobile body 20 which is superior in aesthetic appearance can be obtained.

The maximum value filtering process as the first filtering process may be performed two times or more. More specifically, the maximum value filtering process is repeated multiple times with respect to the same location (source image) of the automobile body 20, and the first filter-processed image is obtained. The minimum value filtering process as the second filtering process is performed a plurality of times with respect to the first filter-processed image. The number of times that the minimum value filtering process is performed is the same as the number of times that the maximum value filtering process is performed.

In this case, any painting defects become more clear in the diagnostic image. More specifically, it can be determined more easily whether or not painting defects exist.

A comparison was made by the present inventor of diagnostic images in which the number of times that the first filtering process and the second filtering process were preformed differed from each other. As a result, it was confirmed that luminance based on painting defects became more clear and distinct when the first filtering process and the second filtering process were performed three times. More specifically, by carrying out the first filtering process and the second filtering process three times each, it becomes easier to determine the presence or absence of painting defects.

In the case that the number of times that the first filtering process and the second filtering process are implemented is one time only, or even in the case of being implemented a plurality of times, the first filtering process may be the minimum value filtering process, and the second filtering process may be the maximum value filtering process. At this time, the second filter-processed image, which is obtained through a two-stage filtering process, is the maximum value filtered-processed image. At this time as well, the same advantages and effects as those discussed above can be obtained.

The present invention is not limited in particular to the embodiments discussed above, and various modifications can be made thereto within a range that does not depart from the spirit and gist of the present invention.

For example, in the event that a defect inspection is performed with respect to a side surface of the automobile body 20, the slit light L may be made to proceed in a horizontal direction.

Further, in the present invention, the object to be inspected is not limited in particular to being a paint material, and the invention may be applied to other coating materials. In this case as well, it is possible to determine whether or not defects exist on the basis of whether or not protuberances are present.

Furthermore, a reflecting mirror may be disposed above the through hole 30, and a location reflected on the reflecting mirror may be photographed by the camera 40.

In addition, it goes without saying that the object to be photographed is not limited to being the automobile 20.

What is claimed is:

1. A defect inspection method of inspecting whether or not a defect exists on an object to be photographed, by irradiating striped illumination with respect to the object to be photographed, and based on an image obtained from the object to be photographed, comprising the steps of:
  irradiating striped illumination on the object to be photographed from a striped illumination irradiating unit;
  photographing, by an image capturing unit, the object to be photographed which is irradiated with the striped illumination, and obtaining a source image;
  obtaining a first filter-processed image by a first filtering process that carries out either one of a maximum value filtering process or a minimum value filtering process with respect to the source image;
  obtaining a second filter-processed image by a second filtering process that carries out a remaining one of the minimum value filtering process or the maximum value filtering process with respect to the first filter-processed image;
  obtaining a difference image in which a difference from the source image is determined using the second filter-processed image as a background image; and
  performing a binarization process with respect to the difference image, and obtaining a binarized image for determining whether or not a defect exists within an imaging range.

2. The defect inspection method according to claim 1, wherein, after having performed the first filtering process a plurality of times, the second filtering process is performed the same number of times as the first filtering process.

3. The defect inspection method according to claim 2, wherein the first filtering process and the second filtering process are performed individually two times or more.

4. A defect inspection apparatus adapted to inspect whether or not a defect exists on an object to be photographed, by irradiating striped illumination with respect to the object to be photographed, and based on an image obtained from the object to be photographed, comprising:
  a striped illumination irradiating unit adapted to irradiate the object to be photographed with striped illumination;
  an image capturing unit adapted to photograph the object to be photographed which is irradiated with the striped illumination;
  an image analysis processing unit adapted to carry out an image analysis process with respect to a source image obtained by the image capturing unit; and
  a displacement device adapted to displace the striped illumination irradiating unit and the image capturing unit;
  wherein the image analysis processing unit is configured to perform a first filtering process to obtain a first filter-processed image by carrying out either one of a maximum value filtering process or a minimum value filtering process with respect to the source image, a second filtering process to obtain a second filter-processed image by carrying out a remaining one of the minimum value filtering process or the maximum value filtering process with respect to the first filter-processed image, a differentiating process to obtain a difference image in which a difference from the source image is determined using the second filter-processed image as a background image, and a binarization process with respect to the difference image.

5. The defect inspection apparatus according to claim 4, wherein the image analysis processing unit, after having performed the first filtering process a plurality of times, performs the second filtering process the same number of times as the first filtering process.

6. The defect inspection apparatus according to claim 5, wherein the image analysis processing unit performs the first filtering process and the second filtering process individually two times or more.

* * * * *